(12) United States Patent
Al-Dhafeeri et al.

(10) Patent No.: US 8,474,313 B2
(45) Date of Patent: Jul. 2, 2013

(54) PROCESS FOR TESTING A SAMPLE OF HYDRAULIC FRACTURING FLUID

(75) Inventors: Abdullah M. Al-Dhafeeri, Northern Sadeer (SA); Abdullah M. Al-Harith, Al-Munirah Camp (SA); Omar A. Al-Fuwaires, Al-Roodah (SA)

(73) Assignee: Saudi Arabian Oil Company, Dhahran (SA)

( * ) Notice: Subject to any disclaimer, the term of this patent is extended or adjusted under 35 U.S.C. 154(b) by 549 days.

(21) Appl. No.: 12/730,195

(22) Filed: Mar. 23, 2010

(65) Prior Publication Data

US 2011/0232368 A1    Sep. 29, 2011

(51) Int. Cl.
*E21B 49/08* (2006.01)
(52) U.S. Cl.
USPC ........................ 73/152.18; 73/865.6
(58) Field of Classification Search
USPC ........................... 73/152.18, 865.6
See application file for complete search history.

(56) References Cited

U.S. PATENT DOCUMENTS

| | | | |
|---|---|---|---|
| 2,618,151 A | 11/1952 | Leas | |
| 4,304,122 A | 12/1981 | Tentor | |
| 4,606,227 A | 8/1986 | Walters | |
| 4,715,212 A | 12/1987 | Johanson | |
| 4,791,822 A | 12/1988 | Penny | |
| 4,922,758 A | 5/1990 | Penny | |
| 4,930,361 A | 6/1990 | Nimberger | |
| 5,018,396 A | 5/1991 | Penny | |
| 5,275,063 A | 1/1994 | Steiger et al. | |
| 5,563,339 A | 10/1996 | Compton et al. | |
| 5,604,300 A | 2/1997 | Sayers et al. | |
| 5,663,121 A | 9/1997 | Moody | |
| 5,899,272 A | 5/1999 | Loree | |
| 6,439,310 B1 | 8/2002 | Scott, III et al. | |
| 7,063,151 B2 | 6/2006 | Nguyen et al. | |
| 7,104,328 B2 | 9/2006 | Phillippi et al. | |
| 7,240,545 B1 | 7/2007 | Jennings | |
| 7,387,161 B2 | 6/2008 | Abass et al. | |
| 2006/0070426 A1 | 4/2006 | Pelletier | |
| 2011/0061525 A1* | 3/2011 | Gray et al. | 92/75 |

OTHER PUBLICATIONS

International Search Report and Written Opinion of the ISA, PCT/US2011/029149, May 20, 2011, pp. 1-6.

* cited by examiner

*Primary Examiner* — Hezron E Williams
*Assistant Examiner* — Paul West
(74) *Attorney, Agent, or Firm* — Abelman, Frayne & Schwab

(57) ABSTRACT

An apparatus and process for testing a sample of a hydraulic fracturing fluid is provided. A small quantity of a fracturing fluid sample to be observed and/or tested is placed in a chamber designed with suitable heat and pressure simulation apparatus. With the sample chamber, the efficacy of the fracturing fluid can be ascertained, improper fracturing fluid compositions and/or mixtures, e.g., caused by human error, can be detected, and contamination of the frac-tank can be determined. The overall apparatus is portable and can be transported to the site of the fracturing fluid tank, thereby allowing testing immediately prior to introduction into the well. The samples in the test chamber can be observed for quality control and quality assurance prior to, or during stimulation and water shutoff treatments in the field.

9 Claims, 4 Drawing Sheets

PROCESS FOR TESTING A SAMPLE OF HYDRAULIC FRACTURING FLUID

RELATED APPLICATIONS

[Not applicable]

BACKGROUND OF THE INVENTION

1. Field of the Invention

This invention relates to a portable apparatus for testing and observing chemical interactions of a fluid sample, and a process for testing fracturing fluids commonly used for oil reservoir and/or water shutoff treatments.

2. Description of Related Art

Hydraulic fracturing, including introduction of proppants in subterranean oil-bearing reservoir rock formations, is a well known procedure to stimulate well production. Typically, the fracturing fluid and proppants are mixed in a mobile storage vessel, e.g., a trailer-mounted fluid storage container known as a "frac-tank," located at the surface near the well site. Chemical additives, including gel polymers and chemical inhibitors, and energizing components such as carbon dioxide and nitrogen gas, are also mixed in the fracturing composition.

After adequate mixing in the frac-tank, the fracturing fluid is pumped via high-pressure lines through the wellhead and down the wellbore. During ideal hydraulic fracturing operations, the fluid passes into the reservoir formation and induces fractures, and petroleum liquid and gas movement from the reservoir rock into the wellbore is increased, thereby enhancing the recovery of hydrocarbons.

Typically, a viscous, surface-mixed stimulation fluid mixture is injected at pressures adequate to create and propagate fractures in the reservoir. The pressures required to pump such stimulation treatments are relatively high, particularly during injection of gelled, thickened fluids that often are used to propel proppant into the fractures. These pumping pressures will often increase during the treatment process.

Furthermore, in order to effectively transport proppant, use of high viscosity gelling compositions is desirable. However, if viscous gelling occurs prematurely, e.g., in the tanks and/or flowlines or otherwise before the fluid is pumped in the well, the fluid introduction rates decrease and excess pressures are encountered. Various chemical inhibitors, such as encapsulated or chemically coated inhibitors, can be mixed into the fluid mixture to provide a time-delayed gelling of the fracturing fluid in order to avoid premature gelling. Other known additives can also be incorporated for the purpose of controlling the gelling rate. For instance, inhibitors to time-delay activation of cross linked polymer gels can be included.

Many stimulation operations are not ideal due to various problems, including limitations associated with mixing of the stimulation fluid and incompatible chemical mixtures. Selection of the appropriate formulation for a fracturing fluid for a given field operation is conventionally a trial-and-error process. In the event that the frac chemicals are not performing properly, premature termination of the fracturing operation is required to prevent conditions dangerous to the personnel and equipment failures such as rupturing of the wellbore casing and other components in hydraulic communication with the fluid source. A premature termination incurs substantial costs and lost time.

In order to minimize the problems associated with conventional hydraulic fracturing operations, quality control and quality assurance analyses are conducted prior to introducing the fracturing composition downhole. Various defects in the frac fluid can be ascertained in these quality control and quality assurance analyses. For instance, the frac tank itself may be contaminated, causing undesirable side reactions of the frac fluid. In other undesirable situations, the frac fluid composition and/or mixture is not what was originally intended, e.g., due to human error in the field.

In actual frac operations at a well site, major equipment and associated potential problems are usually considered, including standby pump trucks and standby blenders. However, quality control programs are desirable because unexpected problems can arise, which are generally much less obvious, and, while they may not terminate the treatment, these problems can ultimately compromise the efficacy of the fracturing operation.

While vendors of frac fluids and their various additives have a working knowledge of most chemical interactions, additive incompatibility nonetheless remains a problem in the industry. For instance, one or more additives may be incompatible with the fracturing fluid, the energizing component, and/or the breaking agents under the prevailing well conditions, i.e., the high temperatures and pressures under which well stimulation occurs.

Quality assurance is undertaken to identify potential problem areas and eliminate them before any problem arises. While many quality assurance and quality control programs rely on various forms and checklists which document the equipment, inventory and instrumentation available on location and after the treatment, materials used and personnel performance, the industry lacks reliable apparatus and a comprehensive protocol to accommodate the requisite testing that is required and which is preferably performed at the drilling site shortly before the frac operation is scheduled to begin.

While many tests can be performed in a laboratory setting, often the actual fluids utilized in the field can differ from the chemicals used in a controlled laboratory environment. For instance, while the aqueous fracturing fluid tested in the laboratory can be supplied directly from the vendor, fracturing fluid use in the field has been sitting in a frac tank and can become contaminated. The quality of the source water can also differ between the field and the laboratory. In addition, the chemicals, additives and other fluids used in the field can be from different product batches than those tested in the laboratory.

Historically, there is been hesitation to conduct actual on-site testing of the frac fluids due to inadequate time and resources to conduct comprehensive tests for each operation. At a minimum, it is desirable to test base fluid properties including viscosity, temperature and pH. It can also be desirable to conduct crosslink time tests. Other tests that can be conducted at the well site include static break tests and time-temperature viscosity profiles. However, these tests may not always accurately approximate the chemical interactions between the various constituents of the frac fluid under the pressure and temperature conditions to which they will be exposed downhole. The lack of actual on-site testing of the frac fluids can result in significant problems in the event that there is a defect in the frac fluid, e.g., contamination of the frac tank, or the frac fluid composition and/or mixture is not what was originally intended, e.g., due to human error in the field.

U.S. Pat. Nos. 5,018,396, 5,275,063, 4,304,122 and 2,618,151 disclose assemblies for testing permeability of materials in simulated environments, including pressure and temperature conditions. However, these assemblies do not solve the problems related to a lack of actual on-site testing of the frac fluids.

Therefore, it is an object of the present invention to provide an apparatus and process for quality control and quality assurance on-site testing of a frac fluid.

It is another object of the present invention to provide such an apparatus that is easily portable and versatile in use.

SUMMARY OF THE INVENTION

The above objects and further advantages are provided by the process of the invention for testing a sample of a hydraulic fracturing fluid. A small quantity of a sample to be observed and/or tested is placed in the chamber by removing the top portion of the chamber. The chamber is designed so that the top and bottom portions can be manually removed. The sample is generally a fracturing fluid (in the form of a single phase fluid, multiple phase fluid, or a gel, where "phase" refers to gases, liquids, or immiscible liquids) drawn from a much larger source, (e.g., a trailer-mounted fluid storage tank), that is conventionally known as a "frac-tank." The samples in the test chamber can be observed for quality control and quality assurance prior to, or during stimulation and water shutoff treatments in the field. With the sample chamber, the efficacy of the fracturing fluid can be ascertained, improper fracturing fluid compositions and/or mixtures, e.g., caused by human error, can be detected, and contamination of the frac-tank can be determined.

The relatively small sample chamber includes a piston closely fit within the chamber that is driven by a pressure source, such as compressed nitrogen gas from a portable nitrogen cylinder. Pressure, e.g., up to about 2000 psi, is applied via the piston to simulate conditions to which the sample chemicals would be exposed in the subterranean reservoir during the fracturing process. One or more suitable pressure gauges are connected to the sample chamber and pressure lines connecting the chamber and the pressure source. The piston is also used for clearing the sample from the chamber, to assist in cleaning the chamber, and/or to purge the chamber of air to avoid contamination.

A heat source such as a length of heating tape having an associated power control is wrapped around the sample chamber to obtain the desired interior temperature, e.g., up to about 300° F, again, to simulate reservoir conditions. A thermometer is included which provides temperature measurements of the chamber's contents.

In other instances, it is desirable to validate the efficacy of the fracturing fluid. After mixing is completed, a sample of the fracturing fluid is tested using the apparatus of the present invention. The sample can be observed to ascertain whether changes in its properties have occurred, e.g. if the fluid separated into layers or precipitated solids.

In addition, the apparatus can be utilized in a laboratory, for instance, to conduct solubility test, gelling tests, corrosion tests, gas sampling, or compression of fluids. With the inclusion of the pressurization of the apparatus and the controlled heating capability, the sample can quickly and conveniently be subjected temperature and pressure conditions that simulate the conditions in the reservoir.

BRIEF DESCRIPTION OF THE DRAWINGS

The invention will be described in further detail below and with reference to the attached drawings in which the same or similar elements are referred to by the same number, and where.

DETAILED DESCRIPTION OF THE INVENTION

Figure 1:
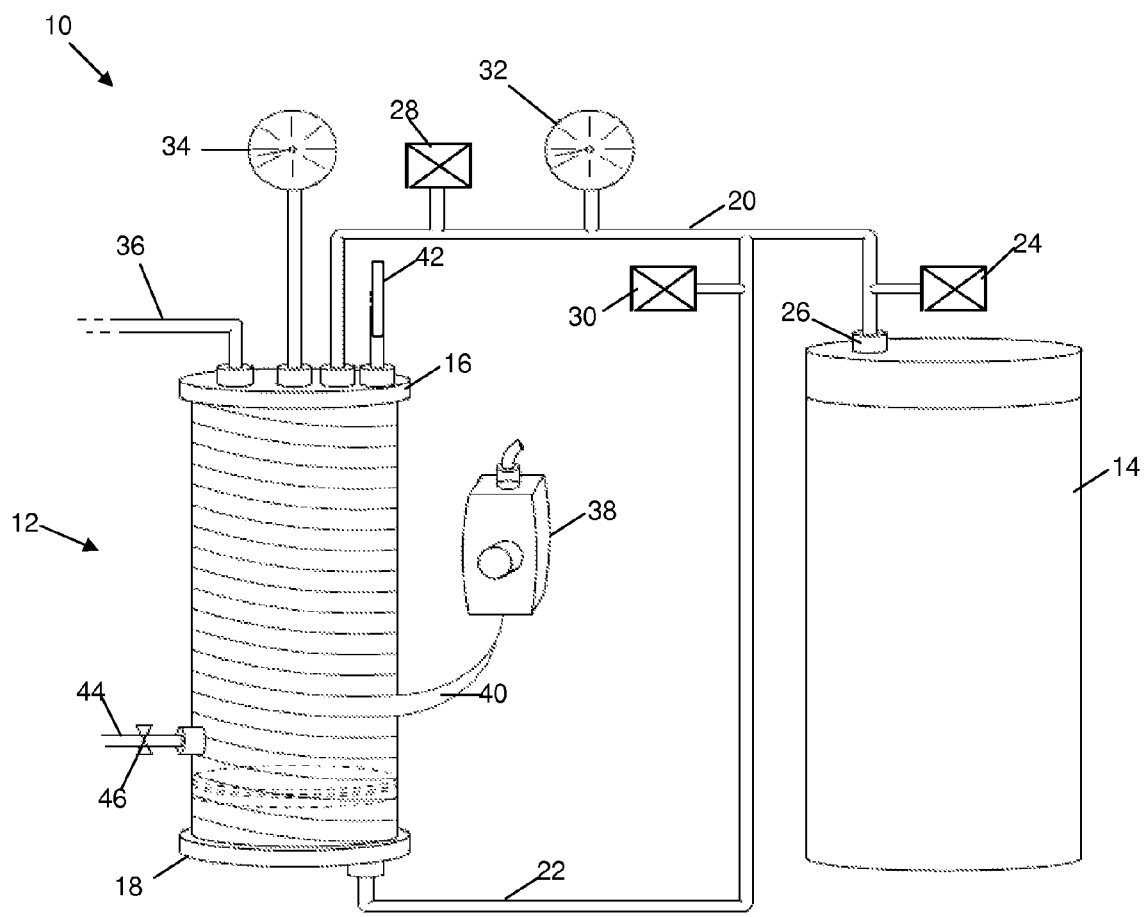
FIG. 1 is an illustration of an apparatus according to one embodiment of the present invention.
Figure 2:
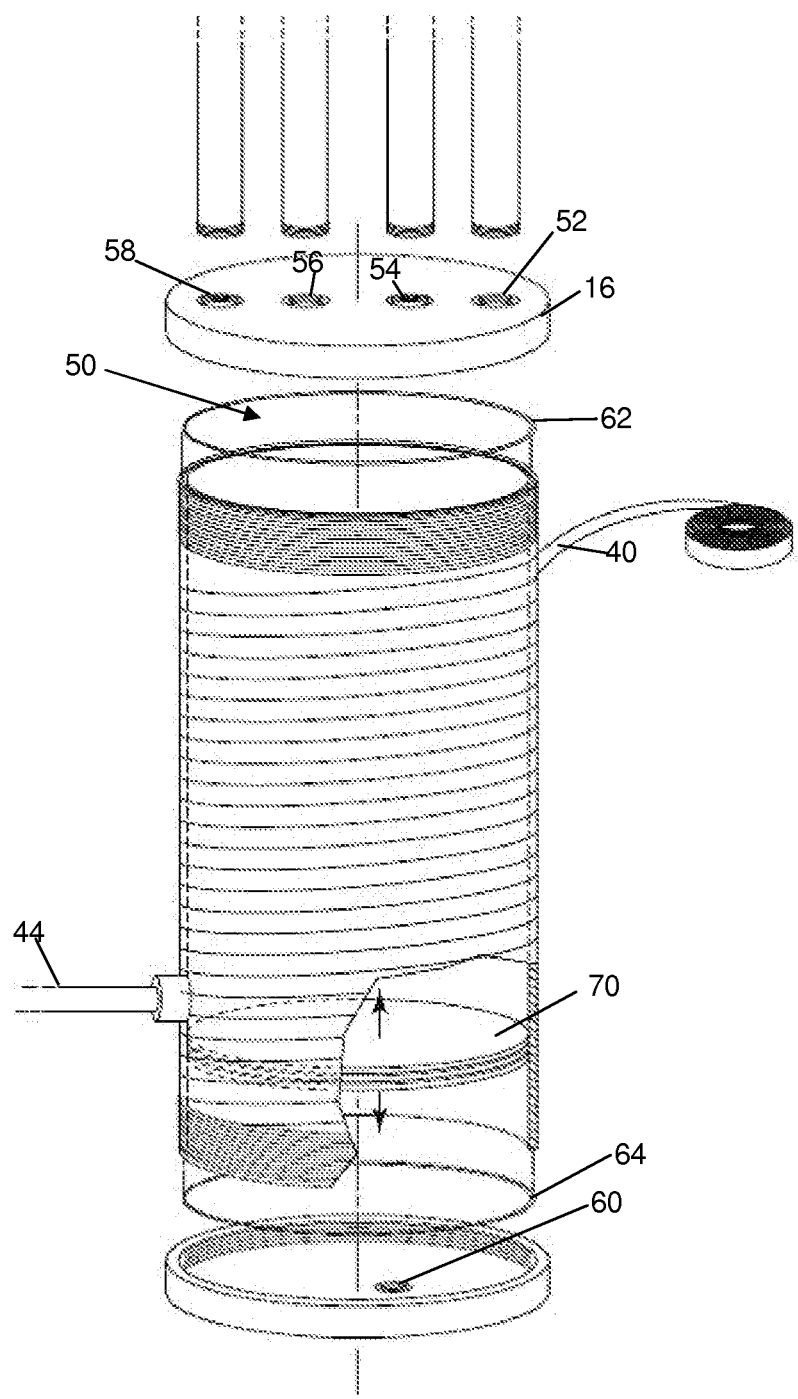
FIG. 2 is an exploded partial cut-away view of the chamber suitable for use in the apparatus of the present invention.
Figure 3:
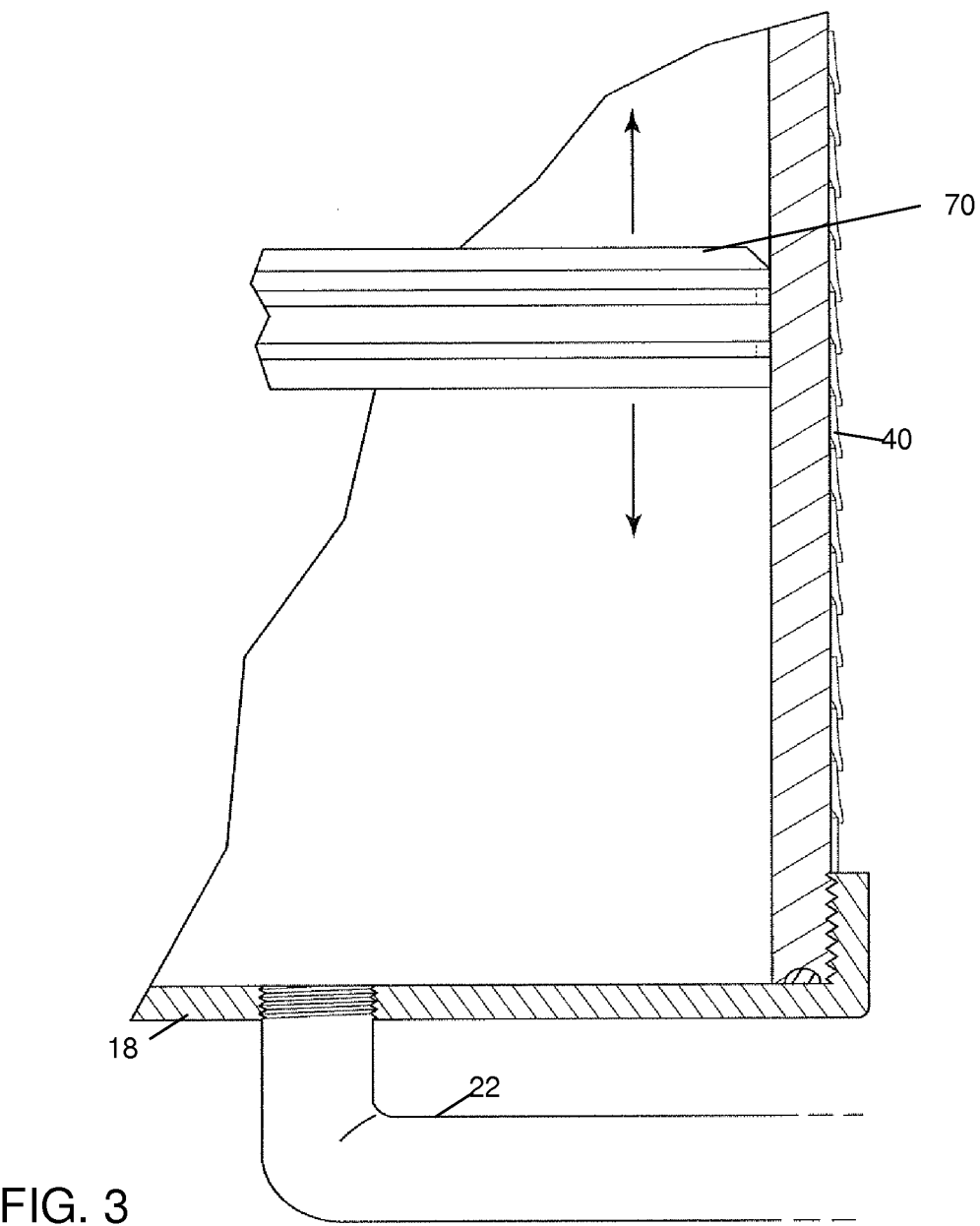
FIG. 3 is an enlarged sectional view depicting the piston within the chamber for use in the apparatus of the present invention.

Referring in general to FIGS. 1-3, an apparatus 10 is illustrated for testing a fracturing fluid used for downhole oil reservoir and/or water shutoff treatments. Apparatus 10 includes a chamber 12 for receiving a sample of fracturing fluid for testing, e.g., from a frac-tank after suitable mixing and prior to downhole introduction. The chamber 12 is in fluid communication with a pressure source 14 via first pressure line 20 passing through a first removable end-cap 16 and a second pressure line 22 passing through a second removable end-cap 18.

A main pressure valve 24 is provided proximate the outlet 26 of the pressure source 14. In addition, a valve 28 is provided along first pressure line 20 and a valve 30 is provided along second pressure line 22. A fluid-tight piston 70 is closely fit within the chamber 12. The piston is driven by gas from line 22 associated with the pressure source 14. Pressure, e.g., up to about 2000 psi, is applied to the contents of the chamber 12 via the piston 70 (FIG. 3) to simulate conditions that the fractioning fluid sample composition would be exposed to in the subterranean reservoir. The piston 70 is also used for clearing the sample from the chamber, to assist in cleaning, and/or to purge the chamber of air to avoid contamination of the sample. The piston 70 provides a pair of variable volume sub-compartments within the chamber 12 that are sealed from one another by one or more suitable sealing structures such as rubber or elastomeric o-rings.

In certain preferred embodiments, chamber 12 has a diameter of about 5 centimeters to about 8 centimeters, and a height of about 20 centimeters to about 40 centimeters; pressure source 14 has a volumetric capacity of about 2 liters to about 3 liters; and the overall apparatus 10 encompasses a maximum area of about 30.5 centimeters by 30.5 centimeters and has a maximum height of about 61 centimeters.

By selective manipulation of valves 24, 28 and/or 30, the user can conveniently select whether pressurized gas is introduced through line 20, line 22, or neither line, depending upon whether pressure is to be applied to the piston to compress the sample or whether pressure is to be applied to the piston 70 to purge the chamber of air and the sample chemicals.

Appropriate gauges are also provided, for instance, along line 20 (gauge 32) and the interior of chamber 12 (gauge 34) through the first removable end-cap 16. In addition, the pressure within the chamber 12 can be reduced by evacuating gas from the pressure source 13 via a relief line 36 and valve. Line 44 and associated valve 46 can be used to collect a sample of the fracturing fluid and/or gas contained within the chamber.

In order to provide thermal control and simulation of the temperature encountered at the downhole location using the apparatus 10, heating system including a temperature controller 38 electrically coupled to length of heat tape 40 is also provided. The heat tape 40 is wrapped around the exterior of the chamber 12 to elevate the temperature, e.g., up to about 300° F. Accordingly, the chamber 12 is formed of a suitable thermally conductive material such as stainless steel, titanium, Hostalloy C or tantalum, which are also inert to the wide range of chemicals to be tested in the chamber. The temperature inside of the chamber 12 is monitored using a temperature gauge 42 such as a thermometer or thermocouple that passes through the first removable end-cap 16. Alternatively, the thermometer and heat tape can be associated with a computer device, such as an integrated circuit, whereby a user can program the desired temperature condition inside chamber 12. In certain embodiments, insulation can be provided surrounding the heat tape 40 to facilitate temperature control and minimize heat loss during the test.

End-cap 16 includes an aperture 52 associated with a tube holding the temperature gauge 42, an aperture 54 associated with the pressure line 20, an aperture 56 associated with the pressure gauge 34 and an aperture 58 associated with the pressure relief outlet 36. End-cap 18 includes an aperture 60 associated with the pressure line 22. Suitable sealing structures, such as elastomeric grommets, are provided at the apertures 52, 54, 56 and 58 for the lines or the temperature gauge passing through the end-caps 16, 18. In addition, O-rings or other suitable seals 62, 64 are provided to maintain the pressure within the chamber 12 for each of the end-caps 16, 18. The end-caps 16, 18 include interior threaded walls that mate with threads on the outside ends of the chamber 12, allowing for convenient assembly and disassembly of the apparatus 10 to introduce materials and/or for cleaning, maintenance or modification of the apparatus.

Figure 4:
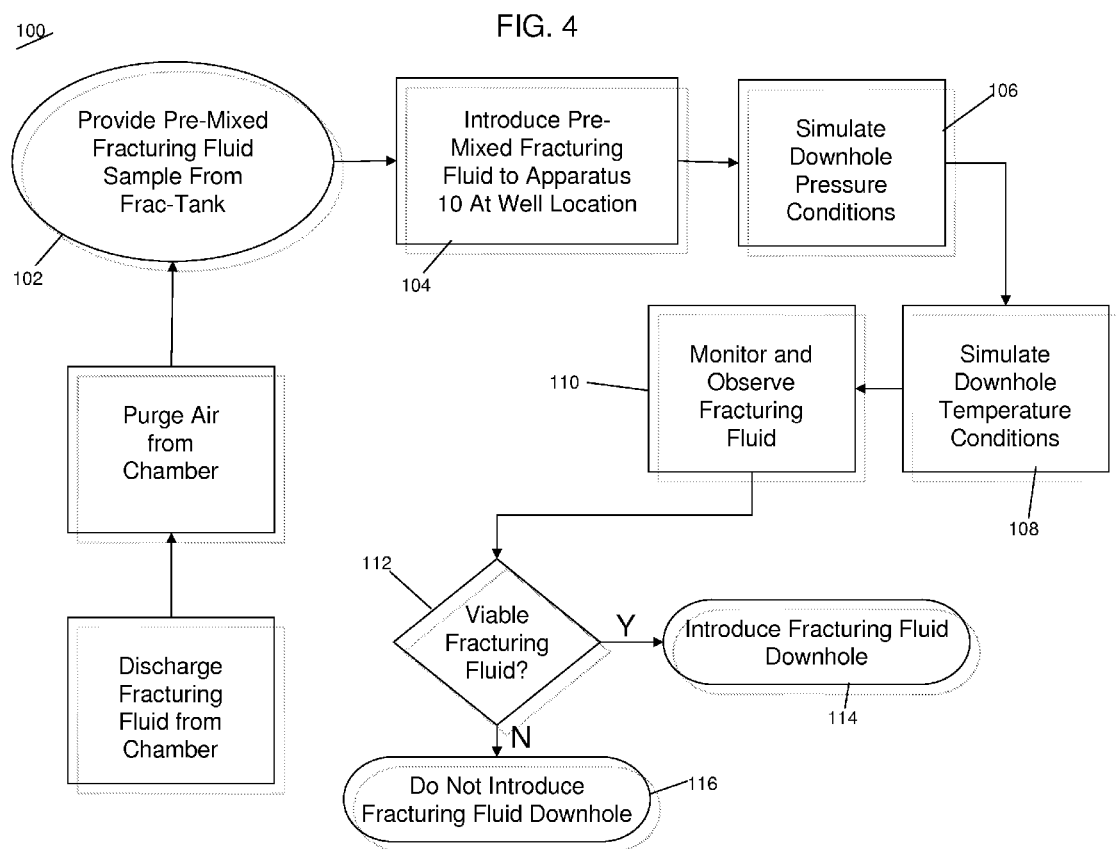
FIG. 4 is a process flow diagram of one method for testing and/or observation according to the present invention using the apparatus shown in FIGS. 1-3.

Referring now to FIG. 4, a process 100 for testing a sample of fracturing fluid using the apparatus 10 is illustrated. At step 102, a relatively small quantity (e.g., about 300 cubic centimeters to about 1000 cubic centimeters) of pre-mixed fracturing fluid from the frac-tank is provided to be observed and/or tested. The sample is introduced into the chamber 12 at step 104 via the open first end 50 of the chamber 12 (FIG. 2). The end-cap 16 is then sealed, and the downhole pressure and temperature conditions within the chamber 12 are simulated. At step 106, pressure is applied via line 20 to displace the piston 70 and thereby compress the contents of the upper compartment of the chamber 12 (e.g., including the sample and any air or inert gas in the compartment). At step 108, the temperature within the chamber is increased to the simulated temperature conditions. As will be understood by one of ordinary skill in the art, the sequence of pressure and temperature change(s) can be varied, or both temperature and pressure can be adjusted at substantially the same time.

At step 110, the sample in the chamber 12 under the simulated temperature and pressure conditions is monitored. Characteristics include viscosity, homogeneity, acidity, phase (e.g., gel or liquid) or a combination of one or more of viscosity, homogeneity, acidity and phase. In addition, the time period of monitoring can be important if the fluid should convert to gel within a period of time in the well for downhole reservoir fracturing and/or water shutoff treatments.

If the sample is determined at step 112 to be a viable sample, the contents of the fluid storage tank from which the sample was drawn can be introduced into the well for downhole reservoir fracturing and/or water shutoff treatments, as indicated at step 114. However, if the sample is determined to be of unsatisfactory quality, the contents of the fluid storage tank from which the sample originated will not be introduced into the well, as indicated at step 114, and will either be modified and re-tested, or discarded.

The sample can be removed as indicated at step 118 by manipulation of piston 70, which can also be used to assist in cleaning and purging the chamber of air to avoid contamination. The end-cap 18 is removed, and pressure applied via line 20 to displace the piston 70 and clear and/or clean the interior of the chamber 12.

The process and apparatus of the present invention have been described above and in the attached drawings; however, modifications will be apparent to those of ordinary skill in the art and the scope of protection for the invention is to be defined by the claims that follow.

The invention claimed is:

1. A process for testing a sample of a hydraulic fracturing fluid comprising:
   a. introducing a sample of hydraulic fracturing fluid of known composition into a sample chamber of a manually portable testing apparatus, the testing apparatus comprising:
      a piston closely fit in the inner chamber region defining a first variable volume compartment of the chamber for receiving the hydraulic fracturing fluid sample and a second variable volume compartment in inversely variable volume
      a source of pressurized fluid in selective fluid communication with the first variable volume compartment and the second variable volume compartment
      a first removable end cap associated with first compartment including a first opening in fluid communication with an evacuation valve, a second opening in fluid communication with a pressure gauge, a third opening in fluid communication with the pressure source, and a fourth opening connected to a temperature gauge,
      a second removable end-cap associated with the second compartment including an opening in fluid communication with the pressure source, and
      a heat source in thermal communication with the inner chamber region;
   b. subjecting the hydraulic fracturing fluid sample to a pressure that simulates the pressure in a subterranean reservoir in which the hydraulic fracturing fluid composition is proposed for use in a hydraulic fracturing operation and monitoring a resultant pressure in the inner chamber region by observing the pressure gauge, the pressure created by introducing pressurized gas from the pressure source and/or reducing excess pressure by opening the evacuation valve;
   c. subjecting the hydraulic fracturing fluid sample to a temperature condition simulating a temperature condition in the subterranean reservoir, the temperature condition controlled by adjusting the heat source and monitoring the temperature in the inner chamber region as measured by the temperature gauge; and
   d. monitoring characteristics including viscosity, homogeneity, acidity, and phase of the hydraulic fracturing fluid or a combination of one or more of viscosity, homogeneity, acidity, and phase of the hydraulic fracturing fluid sample under the simulated reservoir pressure and temperature conditions.

2. The method as in claim 1, wherein the sample chamber is constructed of a heat conducting material and the heat source is a heating tape that is in contact with an outside surface of the sample chamber.

3. The method as in claim 1, further providing a heating chamber to heat inert gas provided from source of inert gas, the heated gas comprising the heat source.

4. The method as in claim 1, further comprising clearing the sample chamber by opening the evacuation valve, removing the second removable end-cap and displacing the piston in a direction toward the position at which the second removable end-cap was located.

5. The method as in claim 1, wherein the pressure source is a container of compressed nitrogen gas.

6. The method as in claim 1, wherein pressure within the sample chamber is increased by operating the pressure source through the opening in the second end-cap to thereby displace the piston to decrease the volume of the inner chamber containing the hydraulic fracturing fluid sample.

7. The method as in claim 1, wherein the simulated temperature conditions are varied during the time of the test.

8. The method as in claim 1, wherein the hydraulic fracturing fluid sample is drawn from a composition mixed in a fracturing tank.

9. The method as in claim 1, wherein the simulated pressure conditions are varied during the time of the test.

* * * * *